US012728227B2

(12) United States Patent
Whittaker

(10) Patent No.: US 12,728,227 B2
(45) Date of Patent: Sep. 8, 2026

(54) FEMALE URINARY CATHETER SYSTEM

(71) Applicant: Garrett Whittaker, Torrington, CT (US)

(72) Inventor: Garrett Whittaker, Torrington, CT (US)

(*) Notice: Subject to any disclaimer, the term of this patent is extended or adjusted under 35 U.S.C. 154(b) by 0 days.

(21) Appl. No.: 18/748,114

(22) Filed: Jun. 20, 2024

(65) Prior Publication Data

US 2024/0335637 A1 Oct. 10, 2024

Related U.S. Application Data

(63) Continuation-in-part of application No. 17/525,854, filed on Nov. 12, 2021, now abandoned.

(51) Int. Cl.
*A61M 25/00* (2006.01)

(52) U.S. Cl.
CPC .... *A61M 25/0017* (2013.01); *A61M 25/0045* (2013.01); *A61M 2025/0056* (2013.01); *A61M 2202/0014* (2013.01); *A61M 2202/0496* (2013.01); *A61M 2205/0205* (2013.01); *A61M 2205/0216* (2013.01); *A61M 2205/0227* (2013.01); *A61M 2205/0233* (2013.01); *A61M 2209/088* (2013.01); *A61M 2210/1085* (2013.01); *A61M 2210/1475* (2013.01)

(58) Field of Classification Search
CPC ........ A61F 5/4408; A61F 5/4556; A61F 5/44; A61F 5/455; A61F 5/4553; A61L 2/101; A61L 2202/111; A61L 2202/24; A61M 2202/0496; A61M 25/0017
See application file for complete search history.

(56) References Cited

U.S. PATENT DOCUMENTS

| | | | | |
|---|---|---|---|---|
| 5,147,301 A * | 9/1992 | Ruvio | A61F 5/451 | 604/97.02 |
| 2008/0051736 A1* | 2/2008 | Rioux | A61L 29/14 | 604/265 |
| 2012/0100187 A1* | 4/2012 | Chappa | A61L 31/16 | 427/2.21 |
| 2016/0166802 A1* | 6/2016 | Ko | A61M 25/0017 | 604/544 |
| 2017/0027347 A1* | 2/2017 | Kovacs | A61L 2/10 | |
| 2017/0216080 A1* | 8/2017 | Moscherosch | A61F 5/443 | |
| 2019/0374213 A1* | 12/2019 | Goldsmith | A61M 27/008 | |
| 2020/0188631 A1* | 6/2020 | Hannon | A61M 25/0045 | |
| 2021/0330369 A1* | 10/2021 | Schwartz | A61F 5/4553 | |

* cited by examiner

*Primary Examiner* — Catharine L Anderson
*Assistant Examiner* — Jihad Dakkak

(57) ABSTRACT

A female urinary catheter system may be provided that utilizes a drainage aperture element having an outer drain edge surrounding an inner drain aperture. The inner drain aperture is coupled to a drainage conduit. The outer drain edge comprises a width dimension larger than that of the drainage conduit. One or more of the outer drain edge, the inner drain aperture, and the drainage conduit may be fabricated from a thermo-responsive polymer. The catheter system may further utilize a catheter conduit coupled to the drainage conduit. The catheter conduit utilizes one or more conduit segments each comprising a first terminal end and a second terminal end. The first terminal end of each conduit segment overlaps the second terminal end of each adjacent conduit segment at respective coupling joints. The catheter system may further utilize an anchor element coupled to the drainage conduit and the catheter conduit.

15 Claims, 6 Drawing Sheets

530A
520
510
to T-joint Conduit
Coupling Element 500A
530B
520
510
to T-joint Conduit
Coupling Element

500B

FEMALE URINARY CATHETER SYSTEM

CROSS-REFERENCE TO RELATED APPLICATIONS

This application claims priority to U.S. Nonprovisional patent application Ser. No. 17/525,854 entitled "Female Urinary Catheter System" filed Nov. 12, 2021 and U.S. Provisional Patent Application Ser. No. 63,112,775 entitled "Female Urinary Catheter System" filed Nov. 12, 2020. The contents of this application are hereby incorporated by reference in their entirety.

BACKGROUND OF THE INVENTION

Urinary catheters are one sector within a larger domestic catheter market that includes cardiovascular catheters, intravenous catheters, neurovascular catheters and the like among other specialty catheters. Within the United States, the larger catheter market is estimated at a value of over $10 billion USD with urinary or urology catheters comprising roughly 20% of that value. Typical urinary catheters are hollow, partially flexible tubes that collect urine from the bladder and lead to one or more drainage bags or other portable or stationary receptacles. Urinary catheters may come in many sizes and types and can be made of rubber, PVC plastic, silicone and the like. Typical types of urinary catheters include those that are inserted into the user's urethral passage to allow for urine to flow therethrough while securely being retained in place by the frictional engagement between the user's urethral passage and the catheter conduit.

Catheters are generally only necessary when a patient can't control the emptying of their bladder. In the case where they cannot empty their bladder, urine will build up and generate pressure in the user's kidneys. Such pressure can lead to failure of kidney function which can result in irreversible damage to the kidneys and may require costly and undesirable chronic dialysis treatments. Most catheters are only necessary until the user regains their ability to urinate on their own which is typically a short period of time. Elderly users and those with a permanent injury, disability or other severe illness may require use of a urinary catheter for a much longer time or even permanently in some cases.

A user may be directed by a doctor to begin using a catheter if they cannot control when they urinate, have urinary incontinence, have urinary retention and the like. Some users may not be able to urinate on their own for reasons including blocked urine flow due to bladder or kidney stones, blood clots in the urine, severe enlargement of the prostate gland, surgery on the prostate gland, surgery in the genital area such as a hip fracture repair or hysterectomy, injury to the nerves of the bladder, a spinal cord injury, a condition that impairs the user's mental function such as dementia, consumption of medications that impair the user's ability for the bladder muscles to squeeze which may cause urine to remain stuck in the bladder and the like, among other reasons.

The typically utilized types of catheters include indwelling catheters, external catheters, and short-term catheters. Indwelling catheters may include urethral catheters and suprapubic catheters. An indwelling catheter is a catheter that resides in the bladder, such as a Foley catheter. This type of catheter may be used for both short and long durations of use. In practice, a nurse typically inserts an indwelling urethral catheter into the user's bladder through the urethra. Alternatively, a healthcare provider may insert the catheter into the bladder through a tiny hole in the abdomen which is referred to as a suprapubic catheter. In the suprapubic case, a tiny balloon at the end of the catheter is inflated with water to prevent the tube from sliding out of the body. The balloon can then deflate when the catheter needs to be removed.

External catheters such as condom catheters are catheters placed outside the body which are typically necessary for male users who, while not having urinary retention problems, have serious functional or mental disabilities such as dementia. In some instances, a device that looks like a condom covers the penis head while a conduit leads from the condom device to a drainage bag. External catheters are generally more comfortable and carry a lower risk of infection than indwelling catheters but they usually need to be changed daily with some models being designed for longer chronic use. Long-term external catheters can cause less skin irritation than those requiring daily removal and reapplication.

In some cases, a short-term catheter, or intermittent catheter, may be desired for a user who may only need a catheter for a short period of time, such as after surgery until the bladder empties. After the bladder empties, it's necessary to remove the short-term catheter and so many healthcare providers refer to this type of catheter as an in-and-out catheter. In the home setting use of intermittent catheters, users may be trained to apply the catheter themselves or with the help of a caregiver. Application can be done through the urethra or through the hole created in the lower abdomen for catheterization.

A catheter-associated urinary tract infection (CAUTI) is known as one of the most common infections a person can contract during a stay in the hospital. Indwelling catheters are the cause of almost all cases of this type of infection. Most commonly, bacteria or fungi may enter the user's urinary tract via the catheter where they may multiply thus causing an infection. However, there are a number of other ways infection can occur during catheterization including the catheter becoming contaminated upon insertion, the drainage bag not being emptied often enough, bacteria from a bowel movement contaminating the catheter, urine in the catheter bag back flowing back into the bladder, the catheter not being cleaned regularly enough and the like.

A CAUTI may exhibit similar symptoms to a typical urinary tract infection (UTI) which include cloudy urine, blood in the urine, strong urine odor, urine leakage around the catheter, pain or discomfort in the lower back or stomach, chills, fever, unexplained fatigue, vomiting and the like. CAUTIs can be difficult to diagnose in if the user is already hospitalized because similar symptoms may be part of the originally diagnosed illness for which hospitalization was required. In the elderly, changes in mental status or confusion can be additional signs of a CAUTI being present.

Upon diagnosis of a CAUTI, prompt treatment is essential as an untreated UTI in general can lead to more serious kidney infections. Additionally, catheter users likely already have preexisting conditions that compromise their immune systems and may have required their use of a catheter in the first place. Moreover, utilizing bodily resources to fight off a CAUTI can cause further immune system stress upon the user which makes the user more vulnerable to additional future infections.

CAUTIs tend to be more resistant to treatment than other UTIs, a common feature in general for hospital-acquired infections. Further, a doctor may prescribe antibiotics to kill off any potentially harmful bacteria causing the infection which places the user at further risk of developing resistance to the given antibiotics. If the infection causes bladder spasms, the doctor may further prescribe an anti-spasmodic to lessen bladder pain.

Generally, indwelling catheters are more risky to the user than externally-applied catheters and so their use would be discouraged relative to that of an externally-applied catheter if all else were equal. However, there do not exist solutions for externally-applied catheters for female users that satisfy the needs of the market and so indwelling catheters are still more commonly used which places the health burden of infectious risk upon the patient along with the associated medical cost burden for treating such infections.

Therefore, it would be advantageous to provide an external catheter that serves the needs of female users. However, common issues with external catheters for females include the poor mechanical coupling of the external catheter to the female users's urinary anatomy. Specifically, a male user's urinary anatomy provides a larger surface area of external structure upon which to secure the external catheter. A female user's urinary anatomy provides significantly less surface area of external structure for the same purpose and so the rate of decoupling of the external catheter from the female's urinary anatomy is significantly higher than that in the case of male user's external catheters.

Consequently, it would be advantageous to provide a female urinary catheter system that provides a female user with a lower rate of decoupling between the external catheter and the urinary anatomy. It would be further advantageous to provide a female user with such a solution that is also portable in nature for those female users who are capable and willing to lead a more active life than those patients who are bedridden. Moreover, it would be advantageous or provide a female urinary catheter system that allows a female user to customize the length and fit of the external catheter to more precisely fit the unique needs of the given female user's body dimensions and urinary anatomy dimensions. Additionally, it would be advantageous to provide a female urinary catheter system that is fabricated from one or more materials that are selected to have one or more of anti-pathogenic properties, antimicrobial properties, antifungal properties, antiviral properties, antibacterial properties and the like or any combination thereof.

DETAILED DESCRIPTION OF THE INVENTION

Before describing the present invention in detail, it is to be understood that the invention is not limited to any one of the particular embodiments, which of course may vary. It is also to be understood that the terminology used herein is for the purpose of describing particular embodiments only, and therefore is not necessarily intended to be limiting. As used in this specification and the appended claims, terms in the singular and the singular forms “a,” “an,” and “the” include plural referents unless the context clearly dictates otherwise. Thus, for example, reference to “a female urinary catheter system” also includes a plurality of female urinary catheter systems and the like.

Figure 1:
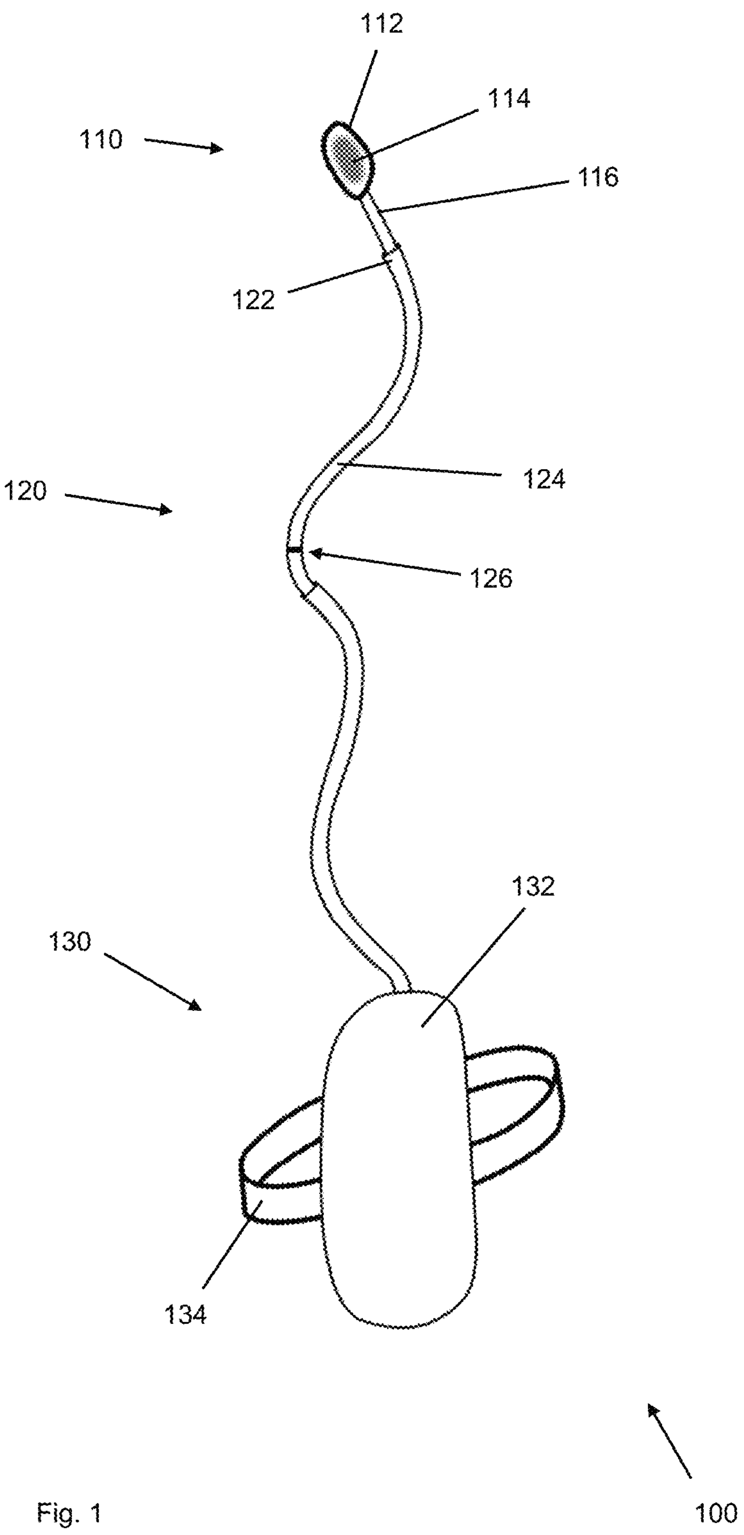
FIG. 1 is an overview of a female urinary catheter system in accordance with some embodiments of the present invention.

Exemplary embodiments of the present invention are illustrated in the accompanying figures. As shown in FIG. 1, an overview of a female urinary catheter system 100 is provided in accordance with some embodiments of the present invention. The female urinary catheter system 100 may comprise a drainage aperture element 110, a catheter conduit 120 and a storage receptacle 130.

The drainage aperture element 110 may comprise an outer drain edge 112 and an inner drain aperture 114 disposed within the outer drain edge 112 that drains through a drainage conduit 116. The outer drain edge 112 may comprise a width dimension larger than that of the drainage conduit 116. As shown in FIG. 1, the outer edge 112 may comprise an oval shape that encircles a similarly shaped inner aperture 114. However, while the outer edge 112 is generally disposed within the same plane when not deformed, the inner aperture 114 may comprise a concave shape relative its operable coupling to the outer edge 112. The concave shape may provide advantageous liquid drainage properties such that any expelled urine that is incident upon the inner surface of the inner aperture 114 may drain towards a central port of the inner aperture 114 that fluidically couples to the catheter conduit 120. In some embodiments, the concave shape may comprise a substantially parabolic shape that causes incident urinary liquid to be directed toward the central port of the inner aperture 114 and down into the catheter conduit 120.

The drainage aperture element 110 may take any suitable shape that conforms to the external urinary anatomy of a female user, but is preferably a flat flexible conformable ring shape or a flat flexible conformable oval shape in order to more easily conform to the external surface of the female user's urinary anatomy. In some embodiments, the outer edge 112 of the drainage aperture element 110 may be customizable and deformable in nature to allow the female user to manipulate the shape of the outer edge 112 to better meet the unique contour of the female user's urinary anatomy. For instance, the outer edge 112 may comprise a thin-gauge gooseneck-type material.

While the inner aperture 114 is preferably concave shaped and more preferably substantially parabolically shaped, the inner aperture 114 may also be flexibly conformable and deformable in nature to allow for a more comfortable fit when worn under tight-fitting clothing. Additionally, such a flexibly conformable and deformable nature would make the female urinary catheter system 100 less noticeable to third-party observers when worn by the female user out in public under clothing such as underwear, pants, dresses and the like.

Additionally, the outer edge 112 of the drainage aperture element 110 may comprise an adhesive disposed between the skin around the urinary anatomy of the female user and the external surface of the outer edge 112. Specifically, the outer edge 112 may comprise the adhesive disposed thereupon prior to application over the female user's urinary anatomy. In other embodiments, the outer edge 112 and/or the inner aperture 114 may comprise a retention band to be worn around the female user's waist and/or legs. In further embodiments, no adhesive or retention band may be utilized, but rather the drainage aperture element 110 may be secured in place via the underwear of the female user being worn thereover.

The catheter conduit 120 may comprise a terminal coupling joint 122 disposed at each end of one or more conduit segments 124 utilized in the catheter conduit 120. The terminal coupling joints 122 may be disposed in frictional coupling engagement to another of the terminal coupling joints 122 of another conduit segment 124. Each of the one or more conduit segments 124 may be modularly coupled to one another and removably coupled to one another. In some embodiments, the conduit segments 124 that are disposed closer to the drainage aperture element 110 may be coupled to an adjacent conduit segment 124 farther from the drainage aperture element 110 in a manner such that the farther conduit segment 124 overlaps the closer conduit segment 124 at the location of the associated terminal coupling joints 122. Such a coupling configuration allows for urinary fluid to flow from the drainage aperture element 110 through the catheter conduit 120 to the storage receptacle 130 without any of the urinary fluid getting caught in the catheter conduit 120 or leaking therefrom.

The catheter conduit 120 may further comprise one or more integrated infection detection systems which may include a series of colorimetric sensors 126 embedded within the catheter conduit 120 and/or drainage aperture element 110 designed to monitor and detect early signs of infection. These colorimetric sensors 126 may be positioned on an inner surface of a conduit to come into contact with the urine flowing through the catheter conduit 120, allowing for visual analysis by the user or healthcare provider. The colorimetric sensors 126 may incorporate pH-sensitive dyes, temperature-sensitive materials, and/or biochemical reaction indicators.

Additionally, the catheter conduit 120 may be fabricated from one or more non-toxic and biocompatible materials. In some embodiments, the non-toxic and biocompatible materials may include, but are not limited to, silicone, foam or other like materials exhibiting soft, deformable, pliable and durable materials such as related polymer materials. Other non-toxic and biocompatible including PVC, polyethylene, polycarbonate, PEEK, polyetherimide, PEI, polypropylene, polysulfone, polyurethane and the like.

Further, the drainage aperture element 110, the catheter conduit 120 and the storage receptacle 130 may be coated with one or more materials having anti-pathogenic properties, antimicrobial properties, anti-fungal properties, antiviral properties and/or antibacterial properties. Such materials may include, but are not limited to, compounds comprising iodine and derivative chemical structures and ions, nano-silver and derivative chemical structures and ions, nano-gold and derivative chemical structures and ions, nano-copper and derivative chemical structures and ions, nano-cobalt and derivative chemical structures and ions, nano-zinc and derivative chemical structures and ions, graphene based compounds, curcumin based compounds and the like or any combinations thereof.

Moreover, the drainage aperture element 110, the catheter conduit 120 and the storage receptacle 130 may comprise one or more illumination elements having anti-pathogenic properties, antimicrobial properties, anti-fungal properties, antiviral properties and/or antibacterial properties. For instance, the one or more illumination elements may comprise LEDs, luminescing materials and coatings and the like or any combination thereof. The one or more illumination elements may emit light within the UV or near-UV spectrum between wavelength ranges including the 200-450 nm band of light.

The catheter conduit 120 may be operably coupled to the storage receptacle 130 to allow transport of urinary fluid thereto. In some embodiments, the catheter conduit 120 may be situated in a position that is vertically above the storage receptacle 130 such that gravity enables transport of the urinary fluid into the storage receptacle 130. In other embodiments, a suction element or fluid pump element may be utilized to generate a low-level vacuum that allows for urinary fluid to be transported from the drainage aperture element 110 to the storage receptacle 130 even when the drainage aperture element 110 is disposed within a vertical plane that is vertically lower than the storage receptacle. Use of the low-level suction would be advantageous even in instances when the drainage aperture element 110 will always be disposed above storage receptacle 130 since the low-level vacuum will aid in the gravity-powered flow of the urinary fluid to comprehensively flow into the storage receptacle 130 and prevent back flow of the urinary fluid back into the female users's bladder which is known to cause urinary tract infections or more serious ailments such as kidney infection or even failure.

The storage receptacle 130 may comprise a urinary fluid reservoir 132 and a coupling mechanism 134. The urinary fluid reservoir 132 may be shaped in any suitable manner but preferably is shaped to contain at least two full bladder movements of the average sized bladder or about 32 ounces. The urinary fluid reservoir may be fabricated from any suitable flexible material that is at least semi-transparent to incident light so as to allow disinfection from external UV or near-UV light emitted from the one or more illumination elements. The coupling mechanism 134 may take any suitable form including, but not limited to, a strap, a buckle, a clasp, hook and loop fasteners, buttons, magnets and the like or any combination thereof.

Figure 2:
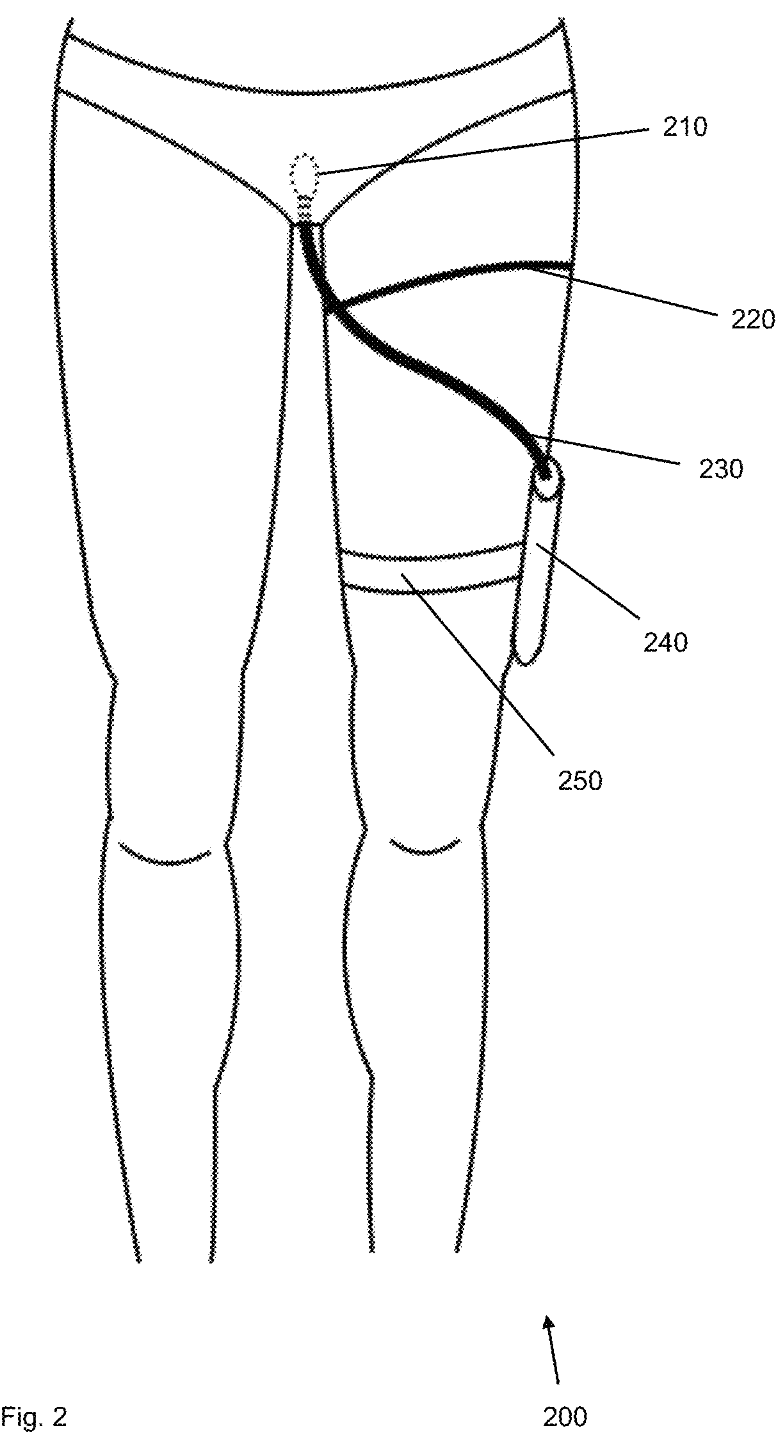
FIG. 2 is an overview of a female urinary catheter system in use by a female user coupled to the female user's leg in accordance with some embodiments of the present invention.

As shown in FIG. 2, an overview of a female urinary catheter system 200 in use by a female user coupled to the female user's leg is provided in accordance with some embodiments of the present invention. The female urinary catheter system 200 may comprise a drainage aperture element 210, a conduit coupling mechanism 220, a catheter conduit 230, a storage receptacle 240 and a coupling mechanism 250. The female urinary catheter system 200 of FIG. 2 may be substantially similar to that of FIG. 1 but for FIG. 2 illustrating the use case of the catheter system 200 in a portable configuration operably coupled to the female user's leg.

It would be advantageous for the female urinary catheter system 200 to comprise a portable configuration in the event the female user is not bedridden and wishes to lead a more active lifestyle. In order to place the catheter system 200 into the portable configuration, the conduit coupling mechanism 220 may be introduced into the system 200 in order to more securely couple the catheter conduit 230 to the female user's body. Without such an additional coupling mechanism, the catheter conduit 230 may move around under the female user's leg while walking around which is not desirable.

Additionally, FIG. 2 illustrates the drainage aperture element 210 being disposed under the female user's underwear and over the female user's urinary anatomy. By securing the catheter conduit 230 to the female user's upper leg, securing the storage receptacle 240 to the female user's lower leg and securing the drainage aperture element 210 under the user's underwear but over the female user's urinary anatomy, the catheter system 200 may remain in a functional configuration as a catheter even while the female user is actively leading their life doing such activities as walking and the like.

Figure 3:
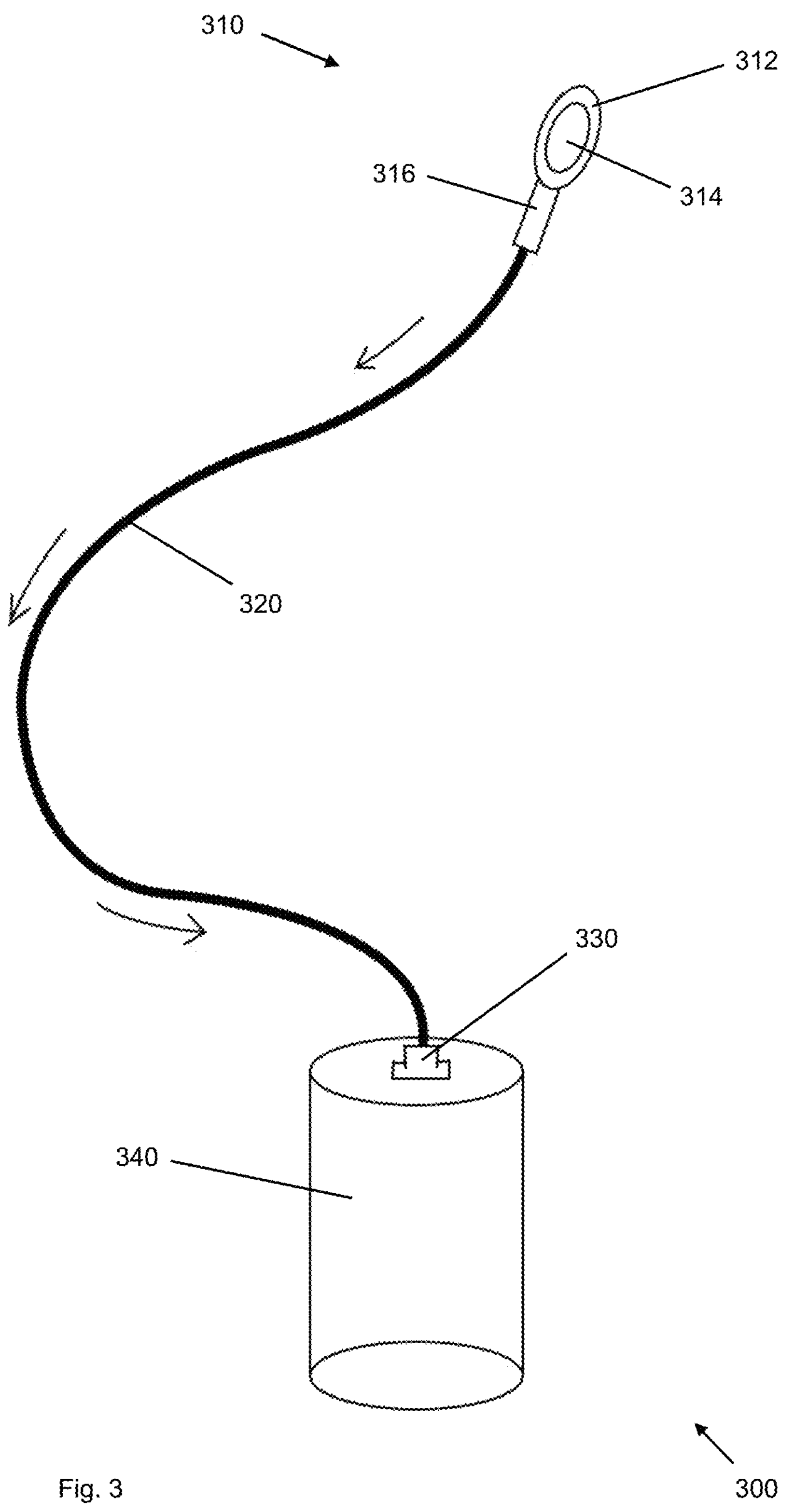
FIG. 3 is an overview of a female urinary catheter system utilizing a portable pump element operably coupled thereto in accordance with some embodiments of the present invention.

As shown in FIG. 3, an overview of a female urinary catheter system 300 utilizing a portable pump element 330 operably coupled thereto is provided in accordance with some embodiments of the present invention. The female urinary catheter system 300 may comprise a drainage aperture element 310, a catheter conduit 320, a portable pump element 330 and a storage receptacle 340.

The drainage aperture element 310 may comprise an outer edge 312, an inner aperture 314 and a coupling joint 316. The coupling joint 316 may removably and modularly couple the outer edge 312 and inner aperture 314 to the catheter conduit 320. The portable pump element 330 may be disposed along any portion of the catheter conduit 320 in order to generate a low-level vacuum therein. Preferably, the portable pump element 330 is disposed at a position adjacent the storage receptacle 340 in order to more easily generate a one-way gravity-assisted flow from the drainage aperture element 310 to the storage receptacle 340. The portable pump element 330 may comprise a wireless energy source such as a rechargeable battery but may also operate via grid power out of a standard wall outlet. The low-level suction of the portable pump element 330 may draw a corresponding low level of power from the power source.

Figure 4:
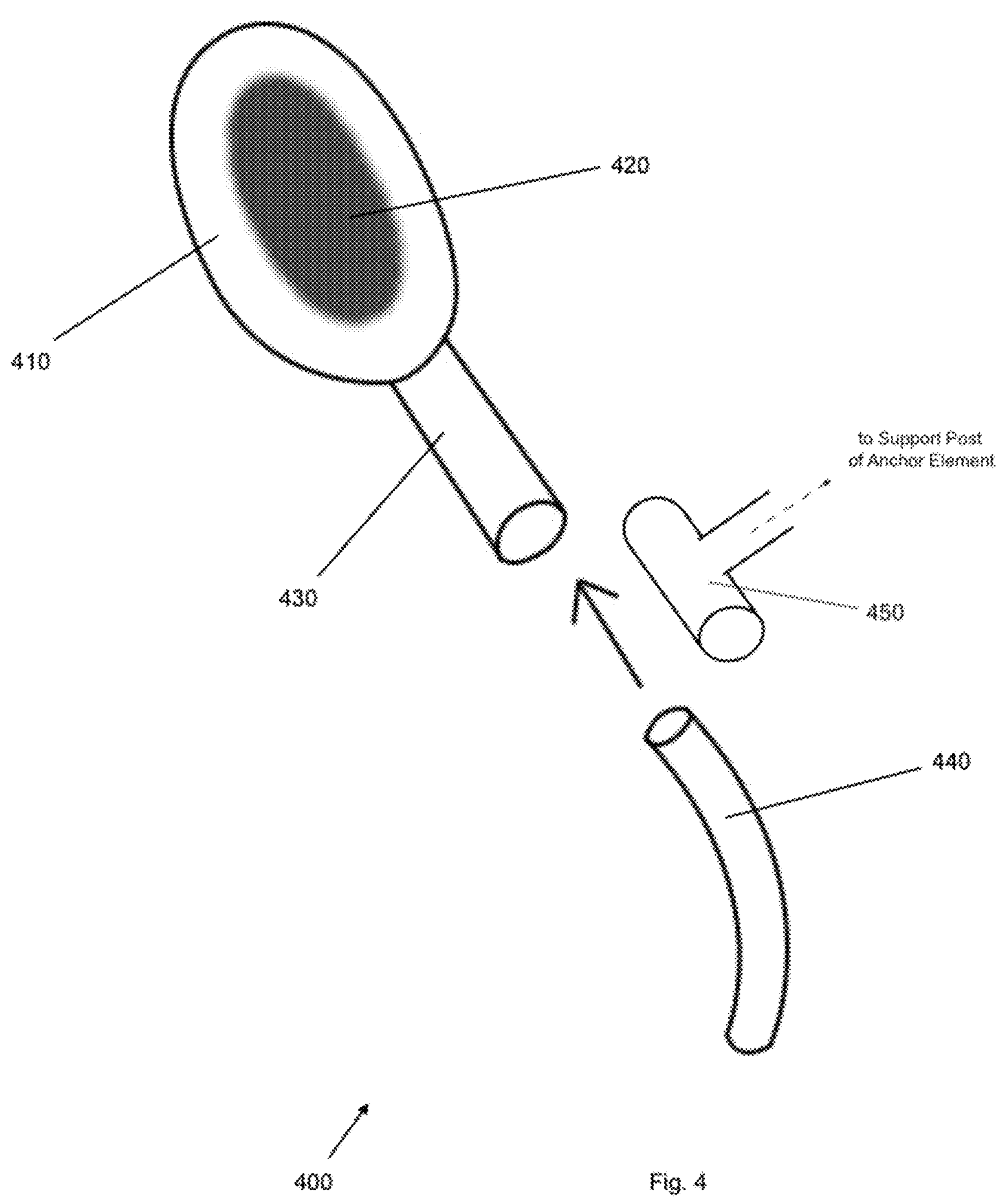
FIG. 4 is an exploded view of a drainage aperture element decoupled from a catheter conduit of a female urinary catheter system in accordance with some embodiments of the present invention.

As shown in FIG. 4, an exploded view of a drainage aperture element 410 and aperture 420 decoupled from a catheter conduit of a female urinary catheter system 400 in accordance with some embodiments of the present invention. Advantageously, the drainage aperture element 410 may comprise a coupling joint 430 that may allow the drainage aperture element 410 to be modularly and removably coupled to one or more of the catheter conduit segments 440. Alternatively, one or more other elements, such as an anchor element described in FIG. 5, may be coupled between the coupling joint 430 and the catheter conduit segment 440. The use of modular components allows the catheter system 400 to be selectively constructed and adjusted by the female user to accommodate various shapes and sizes of female users.

Figures 5A, 5B:
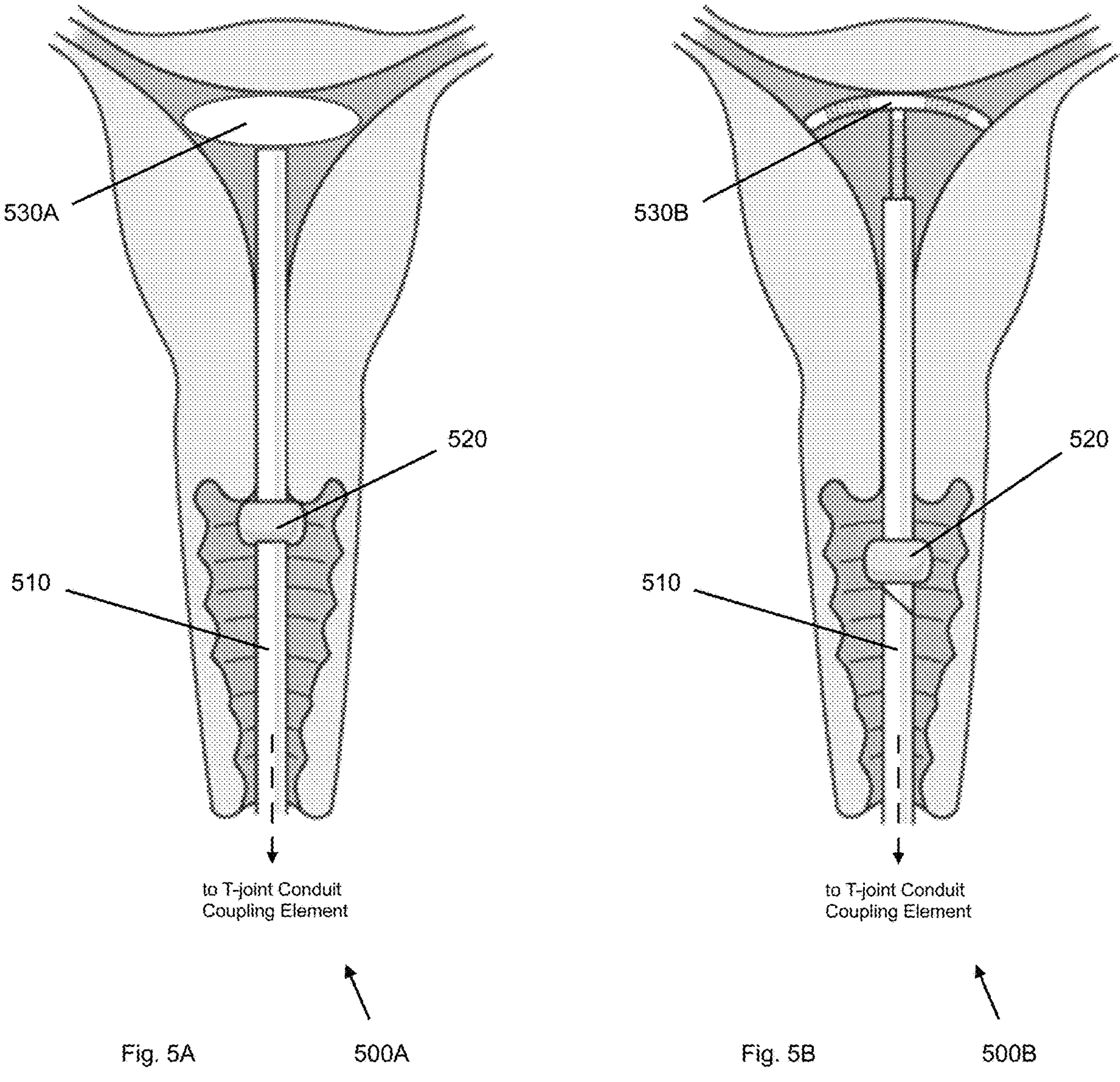
FIG. 5A is a detailed view of an anchor element with a deformable anchor disposed within a female user's uterus of a female urinary catheter system in accordance with some embodiments of the present invention.
FIG. 5B is a detailed view of an anchor element with a t-frame anchor disposed within a female user's uterus of a female urinary catheter system in accordance with some embodiments of the present invention.

As shown in FIG. 5A, a detailed view of an anchor element 500A with a deformable anchor 530A disposed within a female user's uterine or cervical canal of a female urinary catheter system is provided in accordance with some embodiments of the present invention. The anchor element 500A may be disposed between the coupling joint 430 and catheter conduit segment 440 of FIG. 4 by coupling therebetween a T-joint conduit coupling element 450. Further, a support post 510 of the anchor element 500A may be directly coupled to the T-joint conduit coupling 450 and may be used to insert the deformable anchor 530A into the female user's vagina. The T-joint conduit coupling element 450 may comprise a hollow conduit to allow urinary fluid to pass from the coupling joint 430 to the catheter conduit segment 440 but does not allow urinary fluid to pass through the interior of the support post 510 as the support post 510 is not a hollow conduit. This prevents back flow of urinary fluid into the vaginal canal and uterus which would increase the chance of infection. An actuation element 520 may be utilized by the female user to further grip the anchor element 500A and also deploy the deformable anchor 530A into the female user's uterus. In some embodiments, the deployment may include actuating the deformable anchor 530A from a first position within a hollow conduit at the distal end of the support post 510 to a second position disposed external from but coupled to the distal end of the support post 510 and then iteratively returning to either of the first or second positions as desired. In use, the deformable anchor 530A may be used to keep the drainage aperture element in place over the female user's urinary anatomy.

While FIG. 5A illustrates the anchor element 500A being anchored in the uterus, it is understood that the deformable anchor 530A may not be disposed within the female user's uterus at all but rather may be secured against the female user's vaginal canal walls while still achieving the same anchoring function for the female urinary catheter system. In such a vaginal wall configuration, the support post 510 may comprise a shorter length to accommodate the deformable anchor 530A being disposed closer to the T-joint conduit coupling element 450.

As shown in FIG. 5B, a detailed view of an anchor element 500B with a t-frame anchor 530B disposed within a female user's uterine canal of a female urinary catheter system is provided in accordance with some embodiments of the present invention. The anchor element 500B may be disposed between the coupling joint 430 and catheter conduit segment 440 of FIG. 4 by coupling therebetween a T-joint conduit coupling element 450. Further, a support post 510 of the anchor element 500A may be directly coupled to the T-joint conduit coupling 450 and may be used to insert the t-frame anchor 530B into the female user's vagina. An actuation element 520 may be utilized by the female user to further grip the anchor element 500B and also deploy the t-frame anchor 530B into the female user's uterus. In use, the t-frame anchor 530B may be used to keep the drainage aperture element in place over the female user's urinary anatomy. While FIG. 5B illustrates the anchor element 500B being anchored in the uterus, it is understood that the t-frame anchor 530B may not be disposed within the female user's uterus at all but rather may be secured against the female user's vaginal canal walls while still achieving the same anchoring function for the female urinary catheter system.

Figure 6:
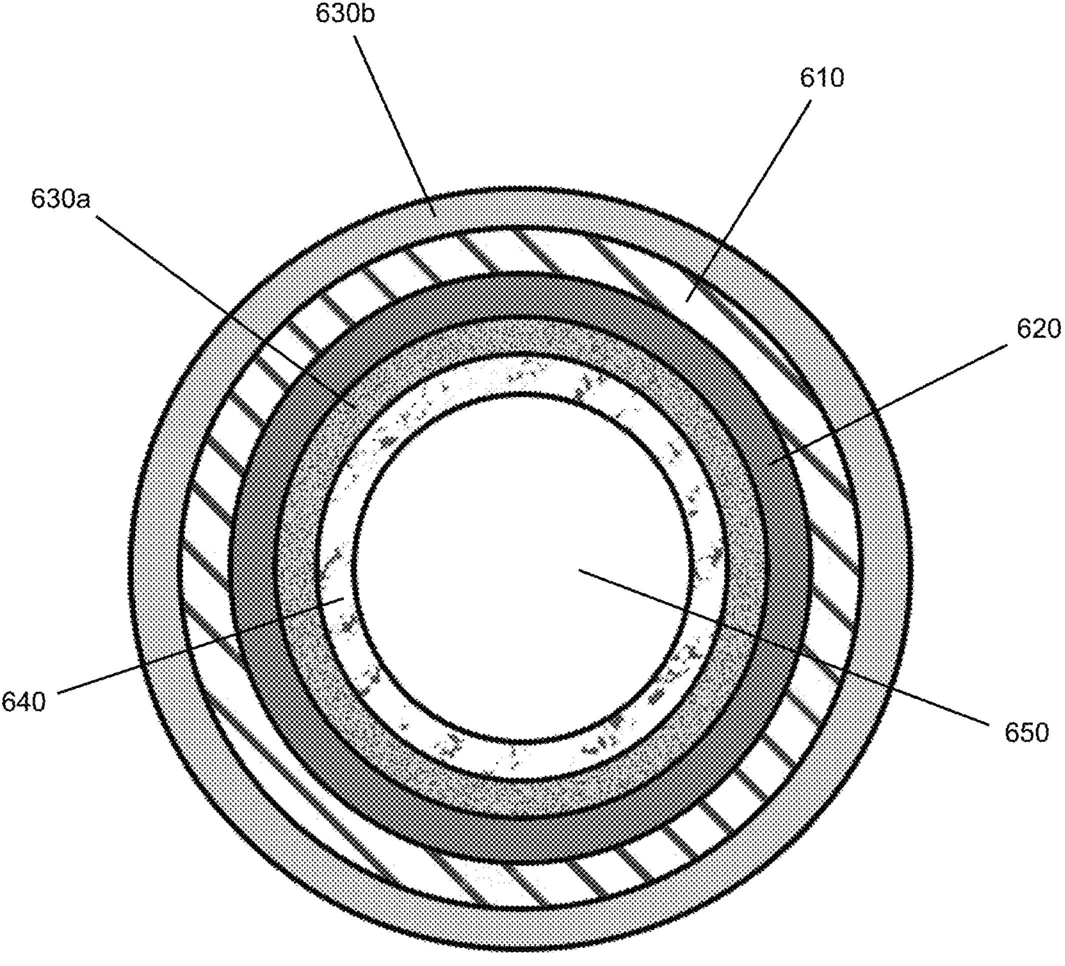
FIG. 6 is a cross-sectional view of a conduit element of a female urinary catheter system having a multilayered structure in accordance with some embodiments of the present invention.

As shown in FIG. 6, a cross-sectional view of a conduit conduit element 600 of a female urinary catheter system having a multilayered structure is provided. The multilayered conduit element 600 may comprise a base structural outer layer 610, a biocompatible inner layer 620, a first hydrophilic layer 630*a*, a second hydrophilic layer 630*b*, and an integrated infection detection system layer 640 which defines an aperture 650 therein. The base structural outer layer 610 may be co-extruded with the biocompatible inner layer 620. The first and second hydrophilic layers 630*a*, 630*b* may be spray or dip-coated onto the co-extruded layers. The integrated infection detection system layer 640 may be inserted within the first hydrophilic layer 630*a*.

The inner layer 620 of the catheter conduit element 600 may be constructed from a soft, pliable silicone elastomer. This material is chosen for its excellent biocompatibility, flexibility, and hypoallergenic properties, which ensure that it is gentle on the user's mucosal tissues, reducing the risk of irritation and discomfort during prolonged use. The silicone elastomer inner layer is designed to conform to the user's anatomy, providing a comfortable and secure fit that adapts to movements without causing friction or pressure points.

Encasing the inner layer 620 may be the outer layer 610 which may be made from a thermo-responsive polymer. The thermo-responsive polymer is selected for its unique ability to change its mechanical properties in response to temperature variations. At lower temperatures, the polymer remains relatively rigid, providing the necessary structural support for the catheter during insertion. Once the catheter is in place and exposed to the user's body temperature, the outer layer becomes more flexible and pliable, enhancing user comfort and reducing the risk of kinking or pressure points.

The first and second hydrophilic layers 630*a*, 630*b* may be composed of materials such as polyvinylpyrrolidone (PVP), polyethylene glycol (PEG), or a copolymer blend of these substances, and may include microencapsulated antimicrobial agents such as silver ions, iodine, chlorhexidine and other like antimicrobial agents listed elsewhere in this disclosure. These agents may be chosen for their broad-spectrum efficacy and ability to disrupt bacterial cell membranes, thereby preventing the growth and spread of pathogens. The microcapsules are designed to remain stable and inert under normal conditions but release their contents upon detecting specific environmental triggers indicative of bacterial presence. These triggers include pH changes, enzymatic activity, and the presence of bacterial toxins.

To apply the first and second hydrophilic layers 630*a*, 630*b* with microencapsulated antimicrobial agents to the interior and exterior surfaces of the inner and outer catheter layers 610, 620, the following process may be employed: 1) A coating solution is prepared by dissolving the hydrophilic polymers (PVP, PEG, or a copolymer blend) in a suitable solvent. The microencapsulated antimicrobial agents are then uniformly dispersed within this solution, ensuring an even distribution of microcapsules throughout the coating material. 2) The catheter layers 610, 620 are submerged in the coating solution for a specified duration, allowing the hydrophilic polymer and microcapsules to adhere to all surfaces. The catheter layers 610, 620 are then removed and allowed to drain, ensuring an even coating layer is formed. 3) Alternatively, the coating solution can be applied to the interior surfaces using a fine spray nozzle designed to reach all internal areas. The catheter components are placed in a controlled environment where the spray-coating can be evenly applied, ensuring the microcapsules are uniformly distributed within the coating layer. 4) Following the application of the coating, the catheter components are subjected to a drying and curing process. This process involves heating the components to a temperature that evaporates the solvent and stabilizes the hydrophilic coating, ensuring the microcapsules remain intact and properly embedded within the polymer matrix.

Once all layers are fully dried and cured, the integrated infection detection system layer 640 may be manually inserted into the aperture 650 so that the layer 640 may be positioned to come into contact with the urine flowing through the catheter layers, allowing for real-time analysis. The infection detection system layer 640 may incorporate pH-sensitive dyes, temperature-sensitive materials, and biochemical reaction indicators.

With reference to FIGS. 1-6, the drainage aperture element of the female urinary catheter system may be utilized as an external catheter in conjunction with an indwelling catheter and/or a suprapubic catheter. Additionally, the uterine anchor element or the vaginal anchor element may be utilized whether or not the drainage aperture element is being utilized complimentary with the indwelling catheter and/or the suprapubic catheter. Any of the aforementioned configurations may be utilized in modular combination with one another as desired by the female user or associated healthcare provider. For instance, a uterine anchor element or a vaginal anchor element may be utilized to anchor the position of the drainage aperture element of an external catheter and/or an indwelling catheter to ensure the functionality of the female urinary catheter system remains robust in the face of most types of movements by the female user.

With reference to FIGS. 1-6, the drainage aperture element may not comprise an outer edge at all but rather may only comprise the inner aperture surrounded by flexible hydrophobic material having an adhesive material disposed along edges thereof for attachment to the urinary anatomy of the female user. Such a configuration would allow for use of disposable one-time-use flexible hydrophobic material elements that may be coupled to the coupling joint or catheter conduit of the female urinary catheter system.

In some embodiments of FIGS. 1-6, the female urinary catheter system may utilize an integrated infection detection system. This system may include a series of sensors embedded within the catheter conduit and/or drainage aperture element designed to monitor and detect early signs of infection. The sensors may be positioned to come into contact with the urine flowing through the catheter, allowing for real-time analysis. The infection detection system may incorporate pH sensors, temperature sensors, and biochemical sensors. The pH sensors may be configured to detect changes in the acidity or alkalinity of the urine, which can indicate the presence of bacterial activity. The temperature sensors may continuously monitor the temperature of the urine, with deviations from the normal range suggesting potential infection or inflammation. Additionally, biochemical sensors may be integrated to detect specific biomarkers associated with urinary tract infections, such as leukocyte esterase and nitrites.

The data collected by these sensors may be processed by a microcontroller embedded within the catheter system. This microcontroller may be equipped with wireless communication capabilities, allowing it to transmit data to an external device, such as a smartphone or a healthcare provider's monitoring system. In the event of detecting abnormal readings, the microcontroller may trigger an alert, notifying the user or healthcare provider of the potential infection. The alert system can be configured to provide visual, auditory, or vibration alerts to the user, ensuring prompt attention to potential issues. For healthcare providers, detailed reports including the sensor data and trends over time can be accessed through a secure online portal, enabling proactive management and timely intervention. The integrated infection detection system may be powered by a small, rechargeable battery housed within any part of the female urinary catheter system, such as the catheter's portable pump element. The battery is designed to last for extended periods, minimizing the need for frequent recharges and ensuring continuous monitoring.

In some embodiments of FIGS. 1-6, the female urinary catheter system may utilize an integrated infection detection system that operates without the use of electronics. This system may include a series of colorimetric sensors embedded within the catheter conduit and drainage aperture element designed to monitor and detect early signs of infection. These sensors may be positioned to come into contact with the urine flowing through the catheter, allowing for visual analysis by the user or healthcare provider.

The infection detection system may incorporate pH-sensitive dyes, temperature-sensitive materials, and biochemical reaction indicators. The pH-sensitive dyes may change color in response to variations in the acidity or alkalinity of the urine, providing a visible indication of bacterial activity. For instance, a change from yellow to blue might indicate an increase in pH, which is often associated with urinary tract infections (UTIs). Temperature-sensitive materials may be integrated into the catheter conduit, which change color based on the temperature of the urine. These materials may shift from one color to another at specific temperature thresholds, indicating potential infection or inflammation when the urine temperature deviates from the normal range. Additionally, biochemical reaction indicators may be incorporated to detect specific biomarkers associated with UTIs, such as leukocyte esterase and nitrites. These indicators may use enzyme-based reactions that produce a distinct color change when in contact with these biomarkers. For example, the presence of leukocyte esterase may cause a colorimetric strip to turn from white to purple. These colorimetric sensors are designed to be easily interpretable, allowing users or healthcare providers to visually inspect the catheter system for signs of infection. The sensors may be placed at key points along the catheter conduit and drainage aperture element to ensure they are exposed to a representative sample of the urine.

In some embodiments of FIGS. 1-6, the female urinary catheter system may utilize elements fabricated from thermo-responsive polymers. For instance, it would be advantageous to utilize such thermo-responsive polymers for any of the conduit elements that may come into contact with the user's body such as, but not limited to, the drainage aperture element 110 and associated component parts 112, 114, 116 of FIG. 1, the drainage aperture element 210 of FIG. 2, the drainage aperture element 310 and associated component parts 312, 314, 316 of FIG. 3, the drainage aperture element 410 of FIG. 4, the support post 510 of FIGS. 5A and 5B, and the outer conduit layer 610 of FIG. 6. These polymers are designed to adjust their rigidity in response to changes in body temperature, thereby enhancing both support and comfort for the user. The thermo-responsive polymers utilized in this system may exhibit a phase transition at a specific temperature range, such as 34 degrees Celsius to 40 degrees Celsius, which is typically around the average human body temperature. The catheter conduit, drainage aperture element, and other relevant components may be manufactured using these advanced polymers. At lower temperatures, such as when the catheter is being handled or inserted, the polymers remain relatively rigid. This rigidity provides the necessary structural support, ensuring ease of insertion and proper placement within the urinary anatomy.

Once the catheter is in place and exposed to the user's body temperature, the thermo-responsive polymers may undergo a phase transition. At body temperature, the polymers become more flexible and conformable. This transition reduces pressure points and enhances comfort, particularly during prolonged use. The flexibility also allows the catheter to better adapt to the user's movements, reducing the risk of irritation and mechanical discomfort. The drainage aperture element, in particular, benefits from this technology. Initially rigid for accurate placement, it becomes soft and pliable once it reaches body temperature, creating a secure and comfortable seal around the urinary anatomy. This dynamic adjustment helps maintain a consistent fit, minimizing the risk of leakage or displacement.

In addition to comfort, the use of thermo-responsive polymers may enhance the catheter's functionality. For instance, the flexibility at body temperature allows the catheter conduit to move more naturally with the user's body, reducing the risk of kinking or blockage. The polymers can be engineered to have specific transition temperatures and mechanical properties, tailored to the needs of different users or use cases. The fabrication process for these thermo-responsive polymers involves blending specific copolymers and additives to achieve the desired thermal and mechanical characteristics. Advanced molding techniques may ensure uniform distribution of the polymers throughout the catheter components, providing consistent performance across different parts of the system. By integrating thermo-responsive polymers into the female urinary catheter system, users are provided with a device that offers enhanced support when needed and superior comfort during extended wear. This concept addresses common issues associated with catheter use, such as discomfort and fit, thereby improving the overall user experience and compliance with catheterization protocols.

In some embodiments of FIGS. 1-6, a female urinary catheter system may utilize a multi-layered catheter conduit (which may be implemented with the catheter conduit 120 of FIG. 1, for instance) designed to optimize both comfort and dynamic adaptability. This catheter conduit may include an inner layer fabricated from a soft, biocompatible material and an outer layer composed of a thermo-responsive polymer. The inner layer of the catheter conduit may be constructed from a soft, pliable silicone elastomer. This material is chosen for its excellent biocompatibility, flexibility, and hypoallergenic properties, which ensure that it is gentle on the user's mucosal tissues, reducing the risk of irritation and discomfort during prolonged use. The silicone elastomer inner layer is designed to conform to the user's anatomy, providing a comfortable and secure fit that adapts to movements without causing friction or pressure points.

Encasing the inner layer may be an outer layer made from a thermo-responsive polymer such as poly(N-isopropylacrylamide) (PNIPAM) or similar copolymers. PNIPAM is particularly suitable due to its lower critical solution temperature (LCST) of approximately 32° C., which is just below human body temperature. This property enables PNIPAM to transition from a flexible, hydrated state at room temperature to a more rigid, dehydrated state at body temperature.

Other materials suitable for the thermo-responsive polymer layer, which exhibit responsiveness when changing temperature from room temperature (approximately 20-25° C.) to body temperature (approximately 37° C.), include: Poly(N-vinylcaprolactam) (PVCL), Poly(ethylene glycol)-b-poly(lactic acid) (PEG-PLA) Copolymers, Poly(oligo(ethylene glycol) methacrylate) (POEGMA) and the like and any combinations thereof. PVCL is a thermo-responsive polymer that undergoes a phase transition around body temperature. At room temperature, PVCL remains relatively rigid, providing structural support for the catheter. As the temperature increases to body temperature, PVCL becomes more flexible and conformable, enhancing comfort and adaptability to the user's movements.

PEG-PLA copolymers exhibit temperature-dependent solubility and mechanical properties. At room temperature, these copolymers provide necessary rigidity and support. When exposed to body temperature, the copolymers transition to a more flexible state, improving user comfort and reducing the risk of pressure points. POEGMA is a thermo-responsive polymer having optimal biocompatibility and phase transition behavior. It remains rigid at room temperature, ensuring ease of insertion and structural integrity. Upon reaching body temperature, POEGMA becomes more flexible, allowing the catheter to adapt to the contours of the user's body, reducing discomfort and irritation.

The thermo-responsive polymer is selected for its unique ability to change its mechanical properties in response to temperature variations. At lower temperatures, the polymer remains relatively rigid, providing the necessary structural support for the catheter during insertion. Once the catheter is in place and exposed to the user's body temperature, the outer layer becomes more flexible and pliable, enhancing user comfort and reducing the risk of kinking or pressure points.

The implementation of this multi-layered design may involve co-extrusion techniques, where both the inner silicone elastomer and the outer thermo-responsive polymer may be simultaneously extruded to form a seamless, integrated catheter conduit. This co-extrusion process ensures a strong bond between the layers, preventing delamination, and maintaining the structural integrity of the catheter. The resulting conduit may have a uniform thickness and consistent properties along its entire length. Additionally, the catheter conduit is treated with a surface modification process to enhance its biocompatibility and reduce bacterial adhesion. This treatment involves the application of a hydrophilic coating that minimizes friction and prevents biofilm formation, further reducing the risk of infections and complications.

The thermo-responsive outer layer's dynamic properties ensure that the catheter provides the required rigidity for insertion and stability but transitions to a softer, more flexible state when in use. This adaptability allows the catheter to better accommodate the user's movements and conform to the contours of the body, enhancing overall comfort during extended wear. The multi-layered catheter conduit is designed to transition smoothly from the drainage aperture element to the storage receptacle, ensuring a continuous, unobstructed flow of urine. The inner silicone layer's flexibility allows it to adapt to the contours of the user's body, while the thermo-responsive outer layer provides dynamic support and comfort under varying temperature conditions.

In some embodiments of FIGS. 1-6, the female urinary catheter system may utilize components fabricated from materials that release antimicrobial agents in response to the presence of bacteria or other pathogens. This system may include a catheter conduit, drainage aperture element, and other relevant components designed to provide targeted antimicrobial protection, enhancing user safety and reducing the risk of infection. The catheter conduit and drainage aperture element may be manufactured using a polymer matrix embedded with microcapsules containing antimicrobial agents such as silver ions, iodine, or chlorhexidine. These antimicrobial agents are chosen for their broad-spectrum efficacy and ability to disrupt bacterial cell membranes, thereby preventing the growth and spread of pathogens.

The microcapsules may be designed to remain stable and inert under normal conditions but release their contents upon detecting specific environmental triggers indicative of bacterial presence. These triggers may include pH changes, enzymatic activity, and the presence of bacterial toxins. The microcapsules can be fabricated using simple and cost-effective techniques such as coacervation or interfacial polymerization, which create a protective shell around the antimicrobial agents.

To implement this design in a cost-effective manner, the following steps may be taken: 1) Utilize low-cost, biocompatible polymers such as polyethylene, polypropylene, and the like or any combination thereof as the base material for the catheter components. 2) Employ scalable microencapsulation techniques like coacervation, which involves phase separation of a polymer solution to form microcapsules around the antimicrobial agents. This method is both economical and efficient, allowing for large-scale production at a minimal cost. 3) During the extrusion or molding process, the polymer matrix may be prepared as a base layer without the microcapsules, focusing on structural integrity and cost efficiency. 4) Apply a cost-effective hydrophilic coating to the catheter components to enhance biocompatibility, reduce bacterial adhesion, and incorporate the microencapsulated antimicrobial agents. This coating can be applied using dip-coating or spray-coating techniques, which are both economical and suitable for high-volume production.

The hydrophilic coating may be composed of materials such as polyvinylpyrrolidone (PVP), polyethylene glycol (PEG), or a copolymer blend of these substances, and will include the microencapsulated antimicrobial agents such as silver ions, iodine, and/or chlorhexidine. These agents may be chosen for their broad-spectrum efficacy and ability to disrupt bacterial cell membranes, thereby preventing the growth and spread of pathogens. The microcapsules are designed to remain stable and inert under normal conditions but release their contents upon detecting specific environmental triggers indicative of bacterial presence. These triggers include pH changes, enzymatic activity, and the presence of bacterial toxins. The hydrophilic coating, integrated with these microcapsules, forms a lubricious, non-fouling surface that inhibits bacterial adhesion and biofilm formation.

To apply the hydrophilic coating with microencapsulated antimicrobial agents to the interior and exterior surfaces of the catheter, the following process may be employed: 1) A coating solution is prepared by dissolving the hydrophilic polymers (PVP, PEG, or a copolymer blend) in a suitable solvent. The microencapsulated antimicrobial agents are then uniformly dispersed within this solution, ensuring an even distribution of microcapsules throughout the coating material. 2) The catheter components, including the interior surfaces, are submerged in the coating solution for a specified duration, allowing the hydrophilic polymer and microcapsules to adhere to all surfaces. The catheter is then removed and allowed to drain, ensuring an even coating layer is formed. 3) Alternatively, the coating solution can be applied to the interior surfaces using a fine spray nozzle designed to reach all internal areas. The catheter components are placed in a controlled environment where the spray-coating can be evenly applied, ensuring the microcapsules are uniformly distributed within the coating layer. 4) Following the application of the coating, the catheter components are subjected to a drying and curing process. This process involves heating the components to a temperature that evaporates the solvent and stabilizes the hydrophilic coating, ensuring the microcapsules remain intact and properly embedded within the polymer matrix. 5) The coated catheters should undergo rigorous quality control tests to ensure uniform coverage, adhesion of the coating, and the integrity of the microencapsulated antimicrobial agents. This step is crucial to verify that the coating process has been successfully implemented and that the antimicrobial properties are effectively integrated.

The antimicrobial agents embedded within the microcapsules may be released in a controlled manner when bacterial presence is detected. For example, the microcapsules containing silver ions may be designed to break down in the acidic environment created by bacterial metabolism, releasing the silver ions and effectively killing the bacteria. This targeted release mechanism ensures that antimicrobial agents are used efficiently, reducing the overall amount needed and thereby lowering material costs. This approach addresses the need for infection prevention in urinary catheter systems without significantly increasing production costs, making it accessible to a wider range of users and healthcare providers.

In some embodiments of FIGS. 1-6, a female urinary catheter system is provided comprising a drainage aperture element comprising an outer drain edge surrounding an inner drain aperture, wherein: the inner drain aperture is coupled to a drainage conduit, the outer drain edge comprises a width dimension larger than that of the drainage conduit, and one or more of the outer drain edge, the inner drain aperture, and the drainage conduit are fabricated from a thermo-responsive polymer; a catheter conduit coupled to the drainage conduit, wherein: the catheter conduit comprises one or more conduit segments each comprising a first terminal end and a second terminal end, the first terminal end of each conduit segment overlaps the second terminal end of each adjacent conduit segment at respective coupling joints, and an infection detection system is disposed adjacent one of the coupling joints; and an anchor element coupled to the drainage conduit and the catheter conduit.

In some embodiments of FIGS. 1-6, the female urinary catheter system comprises a storage receptacle coupled to the catheter conduit, wherein the storage receptacle comprises a leg coupling mechanism, one or more of the drainage aperture element and the catheter conduit comprise a bodily coupling mechanism for coupling around a human body part.

In some embodiments of FIGS. 1-6, one or more of the drainage aperture element, the catheter conduit, and the anchor element comprises chemical structures comprising iodine, one or more of the drainage aperture element, the catheter conduit, and the anchor element comprises chemical structures comprising silver, one or more of the drainage aperture element, the catheter conduit, and the anchor element comprises chemical structures comprising gold, one or more of the drainage aperture element, the catheter conduit, and the anchor element comprises chemical structures comprising copper, one or more of the drainage aperture element, the catheter conduit, and the anchor element comprises chemical structures comprising zinc, one or more of the drainage aperture element, the catheter conduit, and the anchor element comprises chemical structures comprising graphene, one or more of the drainage aperture element, the catheter conduit, and the anchor element comprises chemical structures comprising curcumin, and one or more of the drainage aperture element, the catheter conduit, and the anchor element comprises chemical structures comprising cobalt.

In some embodiments of FIGS. 1-6, one or more of the drainage aperture element, the catheter conduit, the storage receptacle and the anchor element comprises one or more materials having anti-pathogenic properties, antimicrobial properties, anti-fungal properties, antiviral properties, and antibacterial properties.

In some embodiments of FIGS. 1-6, one or more of the drainage aperture element, the catheter conduit and the storage receptacle comprises one or more LEDs that emit light within the wavelength range of 200 to 450 nanometers, and one or more of the drainage aperture element, the catheter conduit and the storage receptacle comprises one or more luminescing materials that emit light within the wavelength range of 200 to 450 nanometers.

In some embodiments of FIGS. 1-6, the catheter conduit comprises a plurality of microencapsulated antimicrobial agents, the catheter conduit comprises polyvinylpyrrolidone, the catheter conduit comprises polyethylene glycol, the catheter conduit comprises a hydrophilic layer and one or more co-extruded layers, and the hydrophilic layer is spray or dip-coated over the co-extruded layers.

In some embodiments of FIGS. 1-6, a female urinary catheter system is provided comprising a drainage aperture element comprising an outer drain edge surrounding an inner drain aperture, wherein: the inner drain aperture is coupled to a drainage conduit, and the outer drain edge comprises a width dimension larger than that of the drainage conduit; a catheter conduit coupled to the drainage conduit, wherein: the catheter conduit comprises one or more conduit segments each comprising a first terminal end and a second terminal end, the first terminal end of each conduit segment overlaps the second terminal end of each adjacent conduit segment at respective coupling joints, and an infection detection system is disposed adjacent one of the coupling joints; and an anchor element coupled to the drainage conduit and the catheter conduit, wherein: the anchor element comprises a deployable anchor that is deployed via translating an actuation element along a support post, and the deployable anchor is secured within a vaginal canal or a cervical canal.

In some embodiments of FIGS. 1-6, a female urinary catheter system is provided comprising a drainage aperture element comprising an outer drain edge surrounding an inner drain aperture, wherein: the inner drain aperture is coupled to a drainage conduit, and the outer drain edge comprises a width dimension larger than that of the drainage conduit; a catheter conduit coupled to the drainage conduit, wherein: the catheter conduit comprises one or more conduit segments each comprising a first terminal end and a second terminal end, the first terminal end of each conduit segment overlaps the second terminal end of each adjacent conduit segment at respective coupling joints, and the catheter conduit comprises a multilayered structure comprising a base structural outer layer, a biocompatible inner layer, and a hydrophilic layer disposed over the base structural outer layer or the biocompatible inner layer; and an anchor element coupled to the drainage conduit and the catheter conduit via a support post terminating into a T-joint conduit coupling element.

Throughout this disclosure, the phrase 'modularly coupled' and similar terms and phrases are intended to convey that any element of a given class of elements may be coupled to another given element and vice versa with equal effect. For example, any extension cord of a plurality of extension cords may be modularly coupled to another extension cord and vice versa with equal effect. Further, throughout this disclosure, the phrase 'removably coupled' and similar terms and phrases are intended to convey that a given element may be iteratively coupled to and removed from another given element as desired. For example, a male plug of a first extension cord may be removably coupled to a female plug of a second extension cord as desired.

The specification and drawings are to be regarded in an illustrative rather than a restrictive sense. However, it will be evident that various modifications and changes may be made thereunto without departing from the broader spirit and scope of the invention as set forth in the claims. Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a," "an," "the," and similar referents in the context of describing the disclosed embodiments (especially in the context of the following claims) are to be construed to cover both the singular and the plural, unless otherwise indicated or clearly contradicted by context. The terms "comprising," "having," "including," and "containing" are to be construed as open-ended terms (i.e., meaning "including, but not limited to,") unless otherwise noted. The term "connected," where unmodified and referring to physical connections, is to be construed as partly or wholly contained within, attached to, or joined together, even if there is something intervening. Recitation of ranges of values are merely intended to serve as a shorthand method of referring individually to each separate value falling within the range, unless otherwise indicated and each separate value is incorporated into the specification as if it were individually recited. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," is understood with the context as used in general to present that an item, term, etc., may be either A or B or C, or any nonempty subset of the set of A and B and C, unless specifically stated otherwise or otherwise clearly contradicted by context. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, the term "plurality" indicates a state of being plural (e.g., "a plurality of items" indicates multiple items). The number of items in a plurality is at least two, but can be more when so indicated either explicitly or by context.

The use of any examples, or exemplary language (e.g., "such as") provided, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described, including the best mode known to the inventors for carrying out the invention. Variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described. Accordingly, the scope of the present disclosure includes all modifications and equivalents of the subject matter recited in the claims appended hereto as permitted by applicable law. Moreover, although above-described elements may be described in the context of certain embodiments of the specification, unless stated otherwise or otherwise clear from context, these elements are not mutually exclusive to only those embodiments in which they are described; any combination of the above-described elements in all possible variations thereof is encompassed by the scope of the present disclosure unless otherwise indicated or otherwise clearly contradicted by context.

All references, including publications, patent applications, and patents, cited are hereby incorporated by reference to the same extent as if each reference were individually and specifically indicated to be incorporated by reference and were set forth in its entirety.

The invention claimed is:

1. A female urinary catheter system, comprising:

a drainage aperture element comprising an outer drain edge surrounding an inner drain aperture, wherein:

the inner drain aperture is coupled to a drainage conduit, the outer drain edge comprises a width dimension larger than that of the drainage conduit, and one or more of the outer drain edge, the inner drain aperture, and the drainage conduit are fabricated from a thermo-responsive polymer;

a catheter conduit coupled to the drainage conduit, wherein:

the catheter conduit comprises a plurality of conduit segments each comprising a first terminal end and a second terminal end, the first terminal end of each conduit segment overlaps the second terminal end of each adjacent conduit segment at respective coupling joints, and the catheter conduit comprises a multilayered structure comprising a base structural outer layer, a biocompatible inner layer, and an infection detection system layer disposed upon the biocompatible inner layer, wherein the base structural outer layer and the biocompatible inner layer are co-extruded together and a hydrophilic coating is disposed upon an inner and outer surface of the co-extruded base structural outer layer and the biocompatible inner layer, wherein the hydrophilic coating comprises iodine microcapsules uniformly dispersed within a copolymer blend of polyvinylpyrrolidone and polyethylene glycol, and the infection detection system layer comprising at least one colorimetric sensor disposed at each of the coupling joints; and an anchor element coupled to the drainage conduit and the catheter conduit.

2. The female urinary catheter system of claim 1, further comprising: a storage receptacle coupled to the catheter conduit, wherein the storage receptacle comprises a leg coupling mechanism.

3. The female urinary catheter system of claim 1, wherein one or more of the drainage aperture element and the catheter conduit comprise a bodily coupling mechanism for coupling around a human body part.

4. The female urinary catheter system of claim 1, wherein one or more of the drainage aperture element, the catheter conduit, and the anchor element comprises chemical structures comprising silver.

5. The female urinary catheter system of claim 1, wherein one or more of the drainage aperture element, the catheter conduit, and the anchor element comprises chemical structures comprising gold.

6. The female urinary catheter system of claim 1, wherein one or more of the drainage aperture element, the catheter conduit, and the anchor element comprises chemical structures comprising copper.

7. The female urinary catheter system of claim 1, wherein one or more of the drainage aperture element, the catheter conduit, and the anchor element comprises chemical structures comprising zinc.

8. The female urinary catheter system of claim 1, wherein one or more of the drainage aperture element, the catheter conduit, and the anchor element comprises chemical structures comprising graphene.

9. The female urinary catheter system of claim 1, wherein one or more of the drainage aperture element, the catheter conduit, and the anchor element comprises chemical structures comprising curcumin.

10. The female urinary catheter system of claim 1, wherein one or more of the drainage aperture element, the catheter conduit, and the anchor element comprises chemical structures comprising cobalt.

11. The female urinary catheter system of claim 1, wherein one or more of the drainage aperture element, the catheter conduit, the storage receptacle and the anchor element comprises one or more materials having anti-pathogenic properties, antimicrobial properties, anti-fungal properties, antiviral properties, and antibacterial properties.

12. The female urinary catheter system of claim 1, wherein one or more of the drainage aperture element, the catheter conduit and the storage receptacle comprises one or more LEDs that emit light within the wavelength range of 200 to 450 nanometers.

13. The female urinary catheter system of claim 1, wherein one or more of the drainage aperture element, the catheter conduit and the storage receptacle comprises one or more luminescing materials that emit light within the wavelength range of 200 to 450 nanometers.

14. A female urinary catheter system, comprising:

a drainage aperture element comprising an outer drain edge surrounding an inner drain aperture, wherein:

the inner drain aperture is coupled to a drainage conduit, and the outer drain edge comprises a width dimension larger than that of the drainage conduit;

a catheter conduit coupled to the drainage conduit, wherein:

the catheter conduit comprises a plurality of conduit segments each comprising a first terminal end and a second terminal end, the first terminal end of each conduit segment overlaps the second terminal end of each adjacent conduit segment at respective coupling joints, the catheter conduit comprises a multilayered structure comprising a base structural outer layer, a biocompatible inner layer, and an infection detection system layer disposed upon the biocompatible inner layer, wherein the base structural outer layer is fabricated from Poly (N-vinylcaprolactam) or Poly (oligo (ethylene glycol) methacrylate) and the biocompatible inner layer is fabricated from a silicone elastomer, and the infection detection system layer comprising a plurality of colorimetric sensors arranged in series at the second terminal end of one of the plurality of conduit segments at each of the coupling joints, wherein each of the colorimetric sensors is covered by the second terminal end of the one of the plurality of conduit segments and by the first terminal end of an adjacent one of the plurality of conduit segments; and an anchor element coupled to the drainage conduit and the catheter conduit, wherein:

the anchor element comprises a deployable anchor that is deployed via translating an actuation element along a support post, and the deployable anchor is secured within a vaginal canal or a cervical canal.

15. A female urinary catheter system, comprising:

a drainage aperture element comprising an outer drain edge surrounding an inner drain aperture, wherein:

the inner drain aperture is coupled to a drainage conduit, and the outer drain edge comprises a width dimension larger than that of the drainage conduit;

a catheter conduit coupled to the drainage conduit, wherein:

the catheter conduit comprises a plurality of conduit segments each comprising a first terminal end and a second terminal end, the first terminal end of each conduit segment overlaps the second terminal end of each adjacent conduit segment at respective coupling joints, and the catheter conduit comprises a multilayered structure comprising a base structural outer layer, a biocompatible inner layer, an outer hydrophilic layer disposed over the base structural outer layer and an inner hydrophilic layer disposed over the biocompatible inner layer, wherein an infection detection system layer is disposed over the inner hydrophilic layer, wherein the infection detection system layer comprises a plurality of colorimetric sensors arranged in series on the inner hydrophilic layer, wherein each of the colorimetric sensors comprise biochemical reaction indicators sensing leukocyte esterase and nitride biomarkers, wherein each of the colorimetric sensors is covered by the second terminal end of the one of the plurality of conduit segments that is overlapped by the first terminal end of an adjacent one of the plurality of conduit segments; and an anchor element coupled to the drainage conduit and the catheter conduit via a support post terminating into a T-joint conduit coupling element.

* * * * *